United States Patent
Rodriguez

[11] 3,949,081
[45] Apr. 6, 1976

[54] 4-CARBAMOYL-1-BENZAZEPINES AS ANTIINFLAMMATORY AGENTS

[75] Inventor: Herman Robert Rodriguez, New York, N.Y.

[73] Assignee: Ciba-Geigy Corporation, Ardsley, N.Y.

[22] Filed: Apr. 8, 1974

[21] Appl. No.: 458,917

[52] U.S. Cl. ............... 424/270; 424/251; 424/263; 424/272; 424/274; 424/275; 424/285
[51] Int. Cl.² ............... A61K 31/42; A61K 31/425
[58] Field of Search ....... 260/239.3 B; 424/270, 272

[56] References Cited
OTHER PUBLICATIONS
J. Org. Chem. 24, 41 (1959).

Primary Examiner—Stanley J. Friedman
Attorney, Agent, or Firm—Joseph G. Kolodny; Theodore O. Groeger; John J. Maitner

[57] ABSTRACT

4-Arylcarbamoyl-2,3,4,5-tetrahydro-1-benzazepine-2,5-diones, e.g. those of the fromula

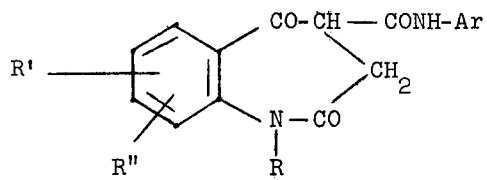

R = H, alkyl or aralkyl
Ar = iso- or heterocyclic aryl
R′,R″ = H, alkyl, alkanoyl, alkoxy, halogen or $CF_3$
alkali metal or acid addition salts thereof are antiinflammatory agents.

4 Claims, No Drawings

4-CARBAMOYL-1-BENZAZEPINES AS ANTIINFLAMMATORY AGENTS

BACKGROUND OF THE INVENTION 2,3,4,5-Tetrahydro-1-benzazepine-2,5-dione-4-carboxylic acids and their alkyl esters have been described by Geissman et al in J. Org. Chem. 24, 41 (1959) as alkaloid-intermediates, and their "rearrangement in aqueous acid and base to 2,4-dihydroxy-quinoline-3-acetic acid" elucidated. Surprisingly it was found that aromatically N-substituted amides of the former acids are highly potent antiinflammatory agents.

SUMMARY OF THE INVENTION

The present invention concerns and has for its object the provision of new 4-arylcarbamoyl-2,3,4,5-tetrahydro-1-benzazepine-2,5-diones, more particularly to those corresponding to the (tautomeric) Formula I

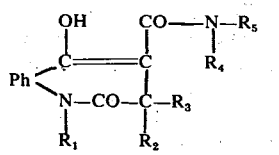

(I)

wherein $R_1$ is hydrogen, lower alkyl or H-Ph-lower alkyl, each of $R_2$, $R_3$ and $R_4$ is hydrogen or lower alkyl, $R_5$ is H-Ph, pyrryl, furyl, thienyl, oxazolyl, thiazolyl, pyridyl, pyrimydyl, benzthiazolyl or lower alkylated or halogenated derivatives of said heterocycles and Ph is unsubstituted 1,2-phenylene, or 1,2-phenylene substituted by at least one member selected from lower alkyl, lower alkanoyl, lower alkoxy, halogeno or trifluoromethyl; or therapeutically useful alkali metal or acid addition salts thereof; as well as of corresponding pharmaceutical compositions and of methods for the preparation and application of these products, which are useful antiinflammatory and antiallergic agents in the treatment or management of arthritic, dermatopathologic, allergic and/or asthmatic conditions.

DESCRIPTION OF THE PREFERRED EMBODIMENTS

The lower alkyl groups $R_1$ to $R_4$, and those of the aromatic radicals $R_5$ and Ph, represent preferably methyl, but also, for example, ethyl, n- or i-propyl or -butyl. The term "lower", referred to above and hereinafter in connection with organic radicals or compounds respectively, defines such with up to 7, preferably up to 4 carbon atoms.

The 1,2-phenylene or phenyl radicals Ph or H-Ph respectively are either unsubstituted, or substituted, preferably by one or two of the same or different members selected from lower alkyl, e.g. those mentioned above; lower alkanoyl, e.g. acetyl, propionyl or pivaloyl; lower alkoxy, e.g. methoxy, ethoxy, n- or i-propoxy or -butoxy; halogeno, e.g. fluoro, chloro or bromo or trifluoromethyl.

Said heterocyclic radicals $R_5$ are preferably unsubstituted, or substituted, for example by one or two of said lower alkyl groups or halogen atoms.

The alkali metal or acid addition salts of said acidic enols or basically substituted derivatives of Formula I are preferably either sodium or potassium enolates, or addition salts of the bases thereof with therapeutically useful acids, e.g. those listed below.

The compounds of the invention exhibit valuable pharmacological properties, primarily anti-inflammatory activity. This can be demonstrated by in-vitro or in-vivo tests, using for the latter advantageously mammals, such as rats or dogs, as test objects. The compounds of the invention can be administered to the animals either enterally, preferably orally, parenterally, e.g. subcutaneously or intravenously, or topically, for example in the from of aqueous or oily solutions or starchy suspensions. The applied dosage may range between about 0.1 and 200 mg/kg/day, preferably between about 1 and 100 mg/kg/day, advantageously between about 5 and 50 mg/kg/day. The tests chosen are among the classical assay methods for said activity, such as the carageenin paw-edema, or adjuvant arthritis test in rats, or more recent tests described by Perper et al in Arthritis Rheum. 17, 47 (1974). There $^{35}$S-labelled rabbit ear cartilage degradation is induced by the nonphagocytic release of neutral proteases from viable human leukocytes. Anti-rheumatic agents prevent this enzyme-release at concentrations correlated with their blood levels usually achieved in man.

Thus, for example, the 8-chloro-1-methyl-4-(2-thiazolylcarbamoyl)-2,3,4,5-tetrahydro-1-benzazepine-2,5-dione, a representative member of the compounds of Formula I, is highly active in rats at p.o. doses as low as 5 mg/kg/day in the paw-edema and adjuvant arthritis essay and it prevents at very low concentrations the $^{35}$S-enzyme release from viable human leukocytes in vitro. Accordingly, the compounds of the invention are useful antiinflammatory agents, for example in the treatment or management of arthritic and dermato-pathologic conditions.

Particularly active in said tests are compounds of Formula I, in which $R_1$ is hydrogen, lower alkyl or H-Ph-lower alkyl, each of $R_2$, $R_3$ and $R_4$ is hydrogen or lower alkyl, $R_5$ is H-Ph, pyrryl, furyl, thienyl, oxazolyl, thiazolyl, pyridyl, pyrimydyl, benzthiazolyl or mono- or di-lower alkylated or halogenated derivatives of said heterocycles and Ph is unsubstituted 1,2-phenylene, or 1,2-phenylene substituted by one or two members selected from lower alkyl, lower alkanoyl, lower alkoxy, halogeno or trifluoromethyl, or therapeutically useful alkali metal or acid addition salts thereof.

Preferred are those compounds of Formula I, wherein each of $R_1$, $R_2$, $R_3$ and $R_4$ are hydrogen or lower alkyl, $R_5$ is H-Ph, pyrryl, furyl, thienyl, oxazolyl, thiazolyl, pyridyl, pyrimydyl, benzthiazolyl or mono- or di-lower alkylated or halogenated derivatives of said heterocycles, and Ph is unsubstituted 1,2-phenylene, or 1,2-phenylene substituted by one or two members selected from lower alkyl, lower alkanoyl, lower alkoxy, halogeno or trifluoromethyl, or therapeutically useful alkali metal or acid addition salts thereof.

Especially valuable and highly active are compounds of Formula II

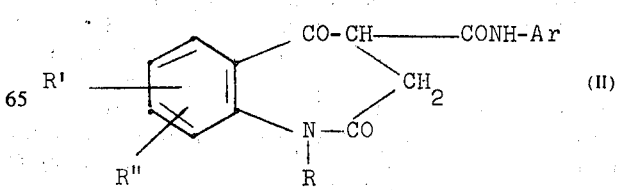

(II)

wherein R is hydrogen or alkyl with up to 4 carbon atoms, each of R' and R'' is hydrogen, alkyl, alkanoyl or alkoxy with up to 4 carbon atoms, fluoro, chloro, bromo or trifluoromethyl, and Ar is unsubstituted phenyl, pyrryl, furyl, thienyl, oxazolyl, thiazolyl, pyridyl, pyrimydyl or benzthiazolyl, or phenyl substituted by R' and R'', or the other heterocyclic radicals substituted by one or two alkyl groups with up to 4 carbon atoms, or therapeutically useful alkali metal or acid addition salts thereof.

Outstanding are those compounds of Formula II, wherein R is hydrogen or methyl, R' is hydrogen, methyl, acetyl, methoxy, fluoro, chloro, bromo or trifluoromethyl, R'' is hydrogen and Ar is R'-phenyl or 2-(thiazolyl, pyridyl or pyrimidyl), or therapeutically useful alkali metal or acid addition salts thereof.

The compounds of the invention are prepared according to methods known per se, for example by;

a. condensing a reactive functional derivative of a corresponding 2,3,4,5-tetrahydro-1-benzazepine-2,5-dione-4-carboxylic acid with an aromatic amine or a salt thereof, more particularly compounds of Formulae III and IV

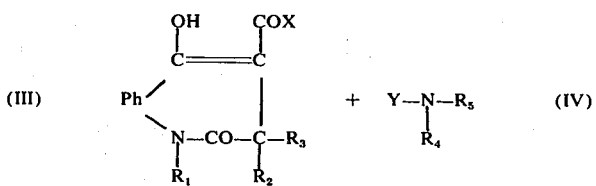

wherein X is lower alkoxy, HPh-alkoxy, amino, halogeno, or acyloxy and Y is hydrogen or an alkali metal atom or b. adding corresponding arylisocyanates to 4-unsubstituted 2,3,4,5-tetrahydro-1-benzazepine-2,5-diones, or tertiary 5-enamines thereof, more particularly reacting compounds of Formulae V and VI

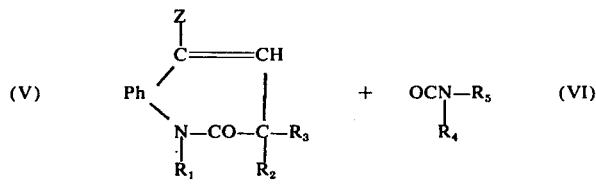

wherein Z is hydroxy, di-lower alkylamino, lower alkyleneimino or monooxa- or -thiaalkyleneimino, and hydrolyzing any resulting enamine and, if desired, converting any resulting compound into another compound of the invention.

The amidation or transamination of said esters, unsubstituted amides, halides, simple or mixed anhydrides of Formula III, the latter, for example, derived from lower alkanoic acids, is carried out in the usual manner, preferably under conditions facilitating the formation of XY. In case it is an alcohol or ammonia, it is preferably eliminated by distillation, or if it is an acid it is preferably neutralized by an inorganic or organic base, for example an alkali or alkaline earth metal hydride, hydroxide, carbonate or bicarbonate; a tri-lower alkylamine or other nitrogen base, e.g. pyridine or quinoline.

The addition of the isocyanates VI to the compounds V, preferably the enamines wherein Z is advantageously pyrrolidino, piperidino, morpholino or thiamorpholino, may occur already under mild conditions, for example by heating in inert solvents, e.g. aliphatic or aromatic hydrocarbons, or in the presence of said basic agents, preferably alkali metal hydrides or tri-lower alkylamines. Any resulting enamine is hydrolyzed under mild acidic conditions, e.g. with diluted aqueous mineral or lower alkanoic acids.

The compounds of the invention so obtained can be converted into each other according to methods known per se. For example, resulting compounds wherein $R_1$ is hydrogen, can be reacted with reactive esters of lower alkanols or H-Ph-alkanols, preferably those derived from hydrohalic, sulfuric, aliphatic or aromatic sulfonic acids, e.g. hydrochloric, hydrobromic, methane-, ethane-, benzene- or p-toluenesulfonic acid. Conversely, any resulting $\alpha$-H-Ph-alkyl, e.g. N-benzyl derivatives, can be hydrogenolyzed, for example, with the use of catalytically activated hydrogen, e.g. hydrogen in the presence of nickel, platinum or palladium catalysts.

A resulting compound can be converted into a corresponding alkali metal enolate or acid addition salt, for example by reacting it with an alkali metal hydride or hydroxide or an inorganic or organic acid respectively, such as a therapeutically useful acid, or with a corresponding anion exchange preparation, and isolating the desired salt. Any resulting salt may be converted into the free compound by treatment with an acid or base until the proper pH has been reached, e.g. an alkali metal hydroxide, ammonia or a hydroxyl ion exchange preparation, or a diluted or weak acid. The salt-forming acids are preferably therapeutically useful acids, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyruvic, phenylacetic, benzoic, 4-aminobenzoic, anthranilic, 4-hydroxybenzoic, salicylic, aminosalicylic, pamoic, nicotinic, methanesulfonic, ethanesulfonic, hydroxy-ethanesulfonic, ethylenesulfonic, benzenesulfonic, halogenbenzenesulfonic, toluenesulfonic, napthalenesulfonic, sulfanilic or cyclohexylsulfamic acid.

These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referrred to in this context, a corresponding salt is also intended, provided such is possible or appropriate under the circumstances.

Resulting mixtures of isomers can be separated into the single isomers by methods in themselves known, e.g. by fractional distillation, crystallization and/or chromatography. Racemic products can likewise be resolved into the optical antipodes, for example by separation of diasteromeric salts or enolesters thereof, e.g. by crystallization of d- or l-tartrates or menthyloxyacetates.

The above reactions are carried out according to standard methods, in the presence or absence of diluents, preferably such as are inert to the reagents and are solvents thereof, of catalysts, condensing or neutralizing agents and/or inert atmospheres, at low temperatures, room temperature or elevated temperatures, at atmospheric or superatmospheric pressure.

The invention also comprises any modification of the above process, wherein a compound resulting as an intermediate at any stage thereof, is used as starting material and the remaining steps are carried out, or the process is discontinued at any stage thereof, or in which the starting material is formed under the reaction conditions or is used in the form of its salts or reactive derivatives. For examples, isocyanates may be formed from the corresponding acid azides and mixed anhydrides from the acids III and simple anhydrides. In the process of the invention, those starting materials are advantageously selected, which yield the above-described preferred embodiments of the invention, especially those corresponding to Formula II.

The starting material used is known or, if new, can be prepared according to the methods described for known analogs thereof, or by the methods illustrated in the examples herein. For example, the derivatives of the acids III can be obtained either by conventional esterification or said conversion into anhydrides or halides, preferably with the use of oxalyl halides.

The pharmacologically active compounds of the invention are useful in the manufacture of pharmaceutical compositions containing an effective amount thereof in conjunction or admixture with excipients suitable for either enteral, parenteral or topical application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) adsorbents, colorants, flavors and sweeteners. Injectable compositions are preferably aqueous isotonic solutions or suspensions, and suppositories are advantageously made from fatty emulsions or suspensions. They may be sterilized and/or contain adjuvants, such as preserving, stabilizing, wetting or emulsifying agents, solution promoters, salts for regulating the osmotic pressure and/or buffers. Said pharmaceutical compositions may also contain other therapeutically valuable substances. They are prepared according to conventional mixing, granulating or coating methods respectively and contain about 0.1 to 75%, preferably about 1 to 50% of the active ingredient.

The following examples are intended to illustrate the invention and are not to be construed as being limitations thereon. Temperatures are given in degrees Centigrade, all parts wherever given are parts by weight, and all evaporations are carried out under reduced pressure.

EXAMPLE 1

The mixture of 23.0 g of 8-chloro-1-methyl-2,3,4,5-tetrahydro-1-benzazepine-2,5-dione-4-carboxylic acid methyl ester, 8.9 g of 2-aminothiazole and 360 ml of toluene is distilled for 20 hours so that after collecting 100 ml of toluene each, this amount is returned to the reaction mixture. It is finally concentrated to a volume of 150 ml, the resulting suspension cooled with ice, filtered and the residue recrystallized from chloroform-acetonitrile, to yield the 8-chloro-1-methyl-4-(2-thiazolylcarbamoyl)-2,3,4,5-tetrahydro-1-benzazepine-2,5-dione of the formula melting at 238°–240°.

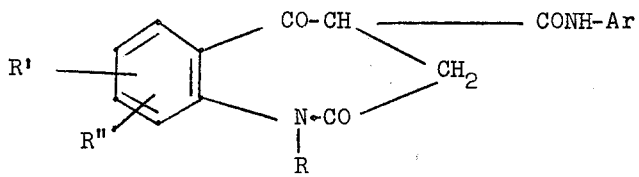

In the above reaction the toluene can be replaced by xylene and the distillation-time restricted to about 7 hours.

The starting material is prepared as follows: Through the suspension of 500 g of 4-chloroanthranilic acid in 3 lt of methanol hydrogen chloride is bubbled for 2 hours while cooling with ice and the mixture refluxed for 10 hours under hydrogen chloride. It is cooled to room temperature, filtered, the filtrate evaporated and the combined residues partitioned between 3 lt of diethyl ether and 4.5 lt of water, the pH of which is adjusted to 10 with 10% aqueous sodium hydroxide. The aqueous layer is extracted 3 times with 2.25 lt of diethyl ether, the combined extracts washed with water, dried, filtered and evaporated, to yield the methyl 4-chloroanthranilate melting at 58°–60°.

Analogously the methyl 5-(fluoro and chloro)-anthranilates are prepared, boiling at 93°/0.35 mm Hg and melting at 65°–67° respectively.

To the solution of 444 g of methyl 4-chloro-anthranilate in 1.3 lt of benzene and 199 ml of pyridine, that of 406 g of 3-carbomethoxy-propionyl chloride in 200 ml of benzene is added dropwise while stirring and cooling with ice. The mixture is stirred for 19 hours at room temperature, filtered and the filtrate evaporated. The combined residues are taken up in 3 lt of chloroform, the solution washed with water, 1 lt of N hydrochloric acid, 1 lt of 10% aqueous sodium bicarbonate and again with water, dried, filtered, evaporated and the residue recrystallized from acetonitrile, to yield the methyl N-(3-carbomethoxypropionyl)-4-chloroanthranilate melting at 80°–84°.

Analogously the 4-unsubstituted, 5-fluorinated and chlorinated derivatives or isomers, are obtained, but the chloroform is replaced by 2.5 lt of ethyl acetate; they melt at 58°–60°, 70°–72° and 100°–103° respectively.

The solution of 264 g of N-(3-carbomethoxypropionyl)-4-chloroanthranilate in 1.8 lt of warm toluene is added dropwise to the hot suspension of 42.6 g of sodium in 900 ml of toluene while stirring and the mixture is refluxed for 5 hours. It is cooled, filtered, the residue taken up in 6 lt of water, the pH of the solution adjusted to 3 with 3N hydrochloric acid, the precipitate formed filtered off, washed with water and recrystallized from acetic acid, to yield the 8-chloro-2,3,4,5-tetrahydro-1-benzazepine-2,5-dione-4-carboxylic acid methyl ester melting at 270°–272°.

Analogously the 8-unsubstituted and the 7-fluorinated and chlorinated derivatives or isomers are obtained, melting at 215°–218°, 230°–232° and 225°–230° respectively.

To the mixture, prepared from the dropwise addition of 131 ml of 1.6 molar n-butyl lithium in hexane to 600 ml of liquid amonia while vigorously stirring under an artificial atmosphere of nitrogen for 40 minutes at −76°, 26.7 g of 8-chloro-2,3,4,5-tetrahydro-1-benzazepine-2,5-dione-4-carboxylic acid methyl ester are added all at once and the solution obtained stirred for 1 hour. Thereupon 14.2 g of methyl iodide are added dropwise and the mixture stirred at −35° for 3 hours. It is conbined with 24 g of ammonium chloride and 600 ml of diethyl ether and the ammonia is allowed to evaporate over night at room temperature. 500 Ml of water are added to the mixture, its pH adjusted to 6–7 with 6N hydrochloric acid, the organic phase separated and the aqueous layer extracted with diethyl ether. The combined organic solutions are washed with water, dried, filtered, evaporated and the residue recrystallized from diethyl ether, to yield the 8-chloro-1-methyl-2,3,4,5-tetrahydro-1-benzazepine-2,5-dione-4-carboxylic acid methyl ester melting at 134°–136°.

Analogously the 8-unsubstituted and the 7-fluorinated and chlorinated derivatives or isomers are obtained, melting at 109°–112° (from benzene-petroleum ether), 147°–149° (from ethyl acetate) and 118°–121° respectively.

EXAMPLE 2

The mixture of 5.0 g of 7-fluoro-1-methyl-2,3,4,5-tetrahydro-1-benzazepine-2,5-dione-4-carboxylic acid methyl ester, 2.3 g of 4-fluoroaaniline and 120 ml of xylene is refluxed under nitrogen for 40 hours, cooled with ice and diluted with 65 ml of petroleum ether. The precipitate formed is filtered off and recrystallized from acetonitrile, to yield the 7-fluoro-1-methyl-4-(4-fluorophenylcarbamoyl)-2,3,4,5-tetrahydro-1-benzazepine-2,5-dione melting at 180°–182°.

EXAMPLE 3

To the boiling suspension of 4.0 g of 2,3,4,5-tetrahydro-1-benzazepine-2,3-dione-4-carboxylic acid methyl ester in 130 ml of xylene, 3.85 g of 4-bromoaniline are added while stirring and the mixture refluxed for 6 hours under nitrogen. It is cooled to room temperature, filtered and the residue recrystallized from acetonitrile-acetic acid, to yield the 4-(4-bromophenylcarbamoyl)-2,3,4,5-tetrahydro-1-benzazepine-2,3-dione melting at 226°–228°.

EXAMPLE 4

According to the methods illustrated by the previous examples, the following compounds of Formula II are obtained from equivalent amounts of the corresponding starting materials. As the case may be, some compounds do not precipitate from the reaction mixture. In these instances the mixture is concentrated or evaporated and the residue recrystallized as indicated in the following Table:

R′ is in 7-position and R″ in 8-position.

| No. | R   | Ar             | R′ | R″ | m.p. °C | recryst. from |
|-----|-----|----------------|----|----|---------|---------------|
| 0   | H   | 4-F—phenyl     | H  | H  | 257–259 | acetic acid   |
| 1   | H   | 4-CF$_3$—phenyl | H  | H  | 218–220 | CH$_3$OH/CH$_3$CN |
| 2   | H   | 4-CH$_3$CO—C$_6$H$_4$ | H | H | 236–238 | ″ |
| 3   | H   | 2-thiazolyl    | H  | H  | 274–276 | acetic acid   |
| 4   | CH$_3$ | ″           | F  | H  | 205–208 | CH$_3$CN/CHCl$_3$ |
| 5   | ″   | ″              | Cl | H  | 251–253 | ″ |
| 6   | ″   | 2-pyridyl      | H  | Cl | 198–200 | ″ |
| 7   | ″   | 4-F—phenyl     | H  | ″  | 205–208 | ″ |
| 8   | ″   | ″              | H  | H  | 208–210 | acetonitrile  |
| 9   | ″   | ″              | F  | H  | 180–182 | ″ |
| 10  | ″   | 4-CF$_3$—phenyl | H  | H  | 205–207 | ″ |
| 11  | ″   | ″              | F  | H  | 194–196 | ″ |
| 12  | ″   | ″              | H  | Cl | 199–200 | ″ |
| 13  | ″   | 2-thiazolyl    | H  | H  | 206–208 | ″ |
| 14  | ″   | 4-Br—phenyl    | H  | H  | 230–232 | CH$_3$OH/CH$_3$CN |

EXAMPLE 5

The mixture of 3.8 g of 8-chloro-1-n-butyl-2,3,4,5-tetrahydro-1-benzazepine-2,5-dione-4-carboxylic acid methyl ester, 1.17 g of 2-aminothiazole and 70 ml of toluene is distilled for 20 hours so that after collecting 25 ml of toluene each, this amount is returned to the reaction mixture. It is finally concentrated to a small volume, the resulting suspension cooled with ice, filtered and the residue recrystallized from chloroform-acetonitrile, to yield the 8-chloro-1-n-butyl-4-(2-thiazolylcarbamoyl)-2,3,4,5-tetrahydro-1-benzazepine-2,5-dione melting at 238° to 240°.

The similarly prepared 1-ethyl-analog melts at 258°–261°.

The starting material is prepared as follows: The suspension of 6.0 g of 8-chloro-2,3,4,5-tetrahydro-1-benzazepine-2,5-dione-4-carboxylic acid methyl ester in 125 ml of dimethyl formamide is added portion-wise to that of 2.1 g of a 57% mineral oil suspension of sodium hydride in 300 ml of dimethylformamide while stirring under argon. After stirring for 3 hours at room temperature 4.6 g of n-butyl iodide are added dropwise and stirring is continued over night at said temperature. The pH of the mixture is adjusted to 2 with 3N hydrochloric acid and the whole evaporated. The residue is partitioned between water and chloroform, the organic solution separated and the aqueous solution extracted with chloroform. The combined extract is washed with water, dried, evaporated and the residue taken up in diethyl ether. The mixture is treated with charcoal, filtered hot and the filtrate concentrated, to yield the 8-chloro-1-n-butyl-2,3,4,5-tetrahydro-1-benzazepine-2,5-dione-4-carboxylic acid methyl ester, melting at 89°–90°.

Similarly the 1-methyl and ethyl-analogs are prepared, as well as the 7-chloro-1-methyl-2,3,4,5-tetrahydro-1-benzazepine-2,5-dione-4-carboxylic acid methyl ester, melting at 134°–136°; 94°–96° and 118°–120° respectively.

EXAMPLE 6

Preparation of 10,000 tablets each containing 50.0 mg of the active ingredient:

Formula 8-chloro-1-methyl-4-(2-thiazolylcarbamoyl)-
2,3,4,5-tetrahydro-1-benzazepine-2,5-dione        500.00 g
Lactose                                            1,706.00 g -continued

| | |
|---|---|
| Corn starch | 90.00 g |
| Polyethylene glycol 6,000 | 90.00 g |
| Talcum powder | 90.00 g |
| Magnesium stearate | 24.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 45 ml of water and the suspension added to the boiling solution of the polyethylene glycol in 180 ml of water. The paste formed is added to the powders which are granulated, if necessary, with an additional amount of water. The granulate is dried overnight at 35°, broken on a screen with 1.2 mm openings and compressed into tablets using concave punches with 7.1 mm diameter, uppers bisected.

I claim:

1. An antiinflammatory pharmaceutical composition comprising an antiinflammatory effective amount of a compound corresponding to the formula

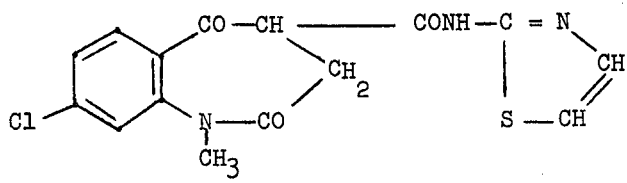

wherein R is hydrogen or alkyl with up to 4 carbon atoms, each of R' and R'' is hydrogen, alkyl, alkanoyl or alkoxy with up to 4 carbon atoms, fluoro, chloro, bromo or trifluoromethyl, and Ar is unsubstituted oxazolyl, thiazolyl, or benzthiazolyi, or said Ar being substituted by one or two alkyl groups with up to 4 carbon atoms, or a therapeutically useful alkali metal or acid addition salt thereof together with a pharmaceutical excipient.

2. A composition as claimed in claim 1, in which formula of the effective compound R is hydrogen or methyl, R' is hydrogen, methyl, acetyl, methoxy, fluoro, chloro, bromo or trifluoromethyl, R'' is hydrogen and Ar is 2-thiazolyl, or a therapeutically useful alkali metal or acid addition salt thereof.

3. A composition as claimed in claim 1, wherein the effective compound is the 8-chloro-1-methyl-4-(2-thiazolylcarbamoyl)-2,3,4,5-tetrahydro-1-benzazepine-2,5-dione.

4. The method of treating inflammatory conditions in a mammal, which consists in administering to said mammal enterally or parenterally a composition as claimed in claim 1.

* * * * *